United States Patent [19]

Berryman et al.

[11] Patent Number: 5,482,960
[45] Date of Patent: Jan. 9, 1996

[54] NONPEPTIDE ENDOTHELIN ANTAGONISTS

[75] Inventors: Kent A. Berryman, Ann Arbor; Amy M. Bunker, Ypsilanti; Annette M. Doherty, Ann Arbor; Jeremy J. Edmunds, Ypsilanti, all of Mich.

[73] Assignee: Warner-Lambert Company, Morris Plains, N.J.

[21] Appl. No.: 339,381

[22] Filed: Nov. 14, 1994

[51] Int. Cl.$^6$ .......................... A61K 31/40; C07D 209/04
[52] U.S. Cl. ............... 514/414; 514/64; 514/80; 514/381; 514/382; 514/418; 548/250; 548/251; 548/252; 548/253; 548/405; 548/412; 548/454; 548/484; 548/485; 548/486; 548/490; 548/491; 548/492; 548/503; 548/504; 548/506; 548/507; 548/511
[58] Field of Search .................................. 548/405, 412, 548/454, 484, 485, 486, 490, 491, 492, 503, 504, 506, 507, 511, 250, 251, 252, 253; 514/64, 80, 381, 414, 418, 382

[56] References Cited

U.S. PATENT DOCUMENTS 5,132,319 7/1992 Girard et al. ......................... 514/415

FOREIGN PATENT DOCUMENTS

| 275667 | 7/1988 | European Pat. Off. ............... 514/415 |
| 0436189 | 12/1990 | European Pat. Off. . |
| WO9308799A1 | 5/1993 | WIPO . |
| WO94/14434 | 7/1994 | WIPO . |

OTHER PUBLICATIONS

Watanabe, T., et al., "Endothelin in Myocardial Infarction," *Nature* (Lond.) 1990;344:114.
Margulies, K. B., et al., "Increased Endothelin in Experimental Heart Failure," *Circulation* 1990;82:2226.
Kon, V., et al., "Glomerular Actions of Endothelin in Vivo," *J. Clin. Invest.* 1989;83:1762.
Perico, N., et al., "Endothelin Mediates the Renal Vasoconstriction Induced by Cyclosporine in the Rat," *J. Am. Soc. Nephrol.* 1990;1:76.
Koshi, T., et al., "Inhibition of Endothelin (ET)–1 and ET–2–Induced Vasoconstriction by Anti–ET–1 Monoclonal Antibody," *Chem. Pharma. Bull.* 1991;39:1295.
Miyamori, I., et al., "Systemic and Regional Effects of Endothelin in Rabbits: Effects of Endothelin Antibody," *Clin. Exp. Pharmacol. Physiol.* 1990;17:691.
Ohno, A. "Effects of Endothelin–Specific Antibodies and Endothelin in Spontaneously Hypertensive Rats," *J. Tokyo Women's Med. Coll.* 1991;61:951.
Lerman, A., et al., "Endothelin has Biological Actions at Pathophysiological Concentrations," *Circulation* 1991;83:1808.
Rodeheffer, R. J., et al., "Circulating Plasma Endothelin Correlates With the Severity of Congestive Heart Failure in Humans," *Am. J. Hypertension* 1991;4:9A.
Arai, H., et al., *Nature* 1990;348:730.
Sakurai, T., et al., *Nature* 1990;348:732.
Lin, H. Y., et al., *Proc. Natl. Acad. Sci.* 1991;88:3185.
Sakamoto, A., et al., *Biochem. Biophys. Res. Chem.* 1991;178:656.
Hosoda, K., et al., *FEBS Lett.* 1991;287:23.
Takayanagi, R., et al., *FEBS Lett.* 1991;282:103.
Panek, R. L., et al., *Biochem. Biophys. Res. Commun.* 1992;183 (2):566.
Saeki, T., et al., *Biochem. Biophys. Res. Commun.* 1991;179:286.
Nakagawa, K. et al., *Nippon Hifuka Gakkai Zasshi* 1990;100:1453–1456.
Noguchi, et al., *Am. Rev. Respir. Dis.* 1992;145 (4 Part 2):A858.
Clark B. A., et al., *Am. J. Obstet. Gynecol.* 1992;166:962–968.
Pittett J., et al,. *Ann Surg.* 1991;213 (3):262.
Gandhi C. B., et al., *Journal of Biological Chemistry* 1990;265 (29):17432.
Collier A., et al., *Diabetes Care* 1992;15 (8):1038.
Basil M. K., et al., *J. Hypertension* 1992;10 (Suppl 4):S49.
Han S. –P., et al., *Life Sci.* 1990;46:767.
Nikolov R. K., et al., *Drugs of Today* 1992;28 (5):303–310.
A. Lerman, et al., *New England J. Med.* 1991;325:997–1001.
K. Kanno, et al., *J. Amer. Med. Assoc.* 1990;264–2868.
M. R. Zamora, et al., *Lancet* 1990;336:1144–1147.
A. Tahara, et al., *Metab. Clin. Exp.* 1991;40:1235–1237.
Stewart, D. J., et al, *Ann. Internal Medicine* 1991;114:464–469.
Yasuda, M., et al., *Amer. Heart J.* 1990;119:801–806.
Stewart, J. T., et al., *Br. Heart J.* 1991;66:7–9.
Lopez–Farre, A., et al., *J. Physiology* 1991;444:513–522.
Stockenhuber, F., et al., *Clin. Sci.* (Lond.) 1992;82:255–258.
Mirua, S., et al., *Digestion* 1991;48:163–172.
Masuda, E., et al., *Am. J. Physiol.* 1992;262:G785–G790.
Murch, S. H., et al., *Lancet* 1992;339:381–384.
Clozel, M., et al., "Pathophysiological role of endothelin revealed by the first orally active endothelin receptor antagonist," *Nature*, 1993;365:759.
Clozel, M. and Watanabe, H., *Life Sci.* 1993;52:825–834.
Stein P. D., et al., "The Discovery of Sulfonamide Endothelin Antagonists and the Development of the Orally Active $ET_A$ Antagonist 5–(Dimethylamino)–N–(3, 4–dimethyl–5–isoxazolyl)–1–naphthalenesulfonamide," *J. Med. Chem.*, 1994;37:329–331.
Elliott, J. D., et al., *J. Med. Chem.*, 1994; 37: 1553–7.
Douglas, S. A., et al., *Circ. Res.*, 1994; 75:190–7.
CA 110: 57508r Preparation . . . Biosynthesis. Gillard et al., p. 674, 1989.
CA 115: 71393j Preparation . . . Agents. Gubin et al., p. 774, 1991.
CA 116: 255478t Preparation . . . Inhibitors. Gillard et al., p. 775, 1992.
CA 117: 191685u Preparation . . . Biosynthesis. Girard et al., p. 784, 1992.
CA 119: 95328 Indoles . . . Transcriptase. Williams et al. 1993.

*Primary Examiner*—Joseph K. McKane
*Attorney, Agent, or Firm*—Elizabeth M. Anderson

[57] ABSTRACT

Novel indole and indoline nonpeptide antagonists of endothelin I are described, as well as novel intermediates used in their preparation, methods for the preparation and pharmaceutical compositions of the same, which are useful in treating elevated levels of endothelin, essential renovascular malignant and pulmonary hypertension, cerebral infarction, cerebral ischemia, congestive heart failure and subarachnoid hemorrhage.

20 Claims, No Drawings

NONPEPTIDE ENDOTHELIN ANTAGONISTS

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, essential renovascular malignant and pulmonary hypertension, cerebral infarction and cerebral ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, benign prosthetic hyperplasia, ischemic disease, gastric mucosal damage, hemorrhagic shock, ischemic bowel disease, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Endothelin is involved in many human disease states.

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-depending manner (Watanabe, T., et al., "Endothelin in Myocardial Infarction," *Nature* (Lond.) 1990;344:114). Thus, ET may be involved in the pathogenesis of congestive heart failure and myocardial ischemia (Margulies, K. B., et al., "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon, V., et al., "Glomerular Actions of Endothelin In Vivo," *J. Clin. Invest.* 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico, N., et al., "Endothelin Mediates the Renal Vasoconstriction Induced by Cyclosporine in the Rat," *J. Am. Soc. Nephrol.* 1990;1:76).

Others have reported inhibition of ET-1 or ET-2-induced vasoconstriction in rat isolated thoracic aorta using a monoclonal antibody to ET-1 (Koshi, T., et al., "Inhibition of Endothelin (ET)-1 and ET-2-Induced Vasoconstriction by Anti-ET-1 Monoclonal Antibody," *Chem. Pharm. Bull.* 1991;39:1295).

Combined administration of ET-1 and ET-1 antibody to rabbits showed significant inhibition of the blood pressure (BP) and renal blood flow responses (Miyamori, I., et al., Systemic and Regional Effects of Endothelin in Rabbits: Effects of Endothelin Antibody," *Clin. Exp. Pharmacol. Physiol.* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno, A. Effects of Endothelin-Specific Antibodies and Endothelin in Spontaneously Hypertensive Rats," *J. Tokyo Women's Med. Coll.* 1991;61:951).

In addition, elevated levels of endothelin have been reported in several disease states (see Table I below).

Burnett and co-workers recently demonstrated that exogenous infusion of ET (2.5 ng/kg/Ml) to anesthetized dogs, producing a doubling of the circulating concentration, did have biological actions (Lerman, A., et al., "Endothelin has Biological Actions at Pathophysiological Concentrations," *Circulation* 1991;83:1808). Thus heart rate and cardiac output decreased in association with increased renal and systemic vascular resistances and antinatriuresis. These studies support a role for endothelin in the regulation of cardiovascular, renal, and endocrine function.

In congestive heart failure in dogs and humans, a significant 2- to 3-fold elevation of circulating ET levels has been reported (Rodeheffer, R. J., etal., "Circulating Plasma Endothelin Correlates With the Severity of Congestive Heart Failure in Humans," *Am. J. Hypertension* 1991;4:9A).

The distribution of the two cloned receptor subtypes, termed $ET_A$ and $ET_B$, have been studied extensively (Arai, H., et al., *Nature* 1990;348:730, Sakurai, T., et al., *Nature* 1990;3 48:732). The $ET_A$, or vascular smooth muscle receptor, is widely distributed in cardiovascular tissues and in certain regions of the brain (Lin, H. Y., et al., *Proc. Natl. Acad. Sci.* 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto, A., et al., *Biochem. Biophys. Res. Chem.* 1991;178:656, Hosoda, K., et al., *FEBS Lett.* 1991;287:23). The $ET_A$ receptor clearly mediates vasoconstriction and there have been a few reports implicating the $ET_B$ receptor in the initial vasodilatory response to ET (Takayanagi, R., et al., *FEBS Lett.* 1991;282:103). However, recent data has shown that the $ET_B$ receptor can also mediate vasoconstriction in some tissue beds (Panek, R. L., et al., *Biochem. Biophys. Res. Commun.* 1992;183(2):566).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1,3,11,15-Ala] and truncated analogs ET[6-21,1,3,11,15-Ala], ET [8-21,11,15-Ala], and N-Acetyl-ET[10-21,11,15-Ala] caused vasorelaxation in isolated, endothelium-intact porcine pulmonary arteries (Saeki, T., et al., *Biochem. Biophys. Res. Commun.* 1991;179:286). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa, K. et al., *Nippon Hifuka Gakkai Zasshi* 1990;100:1453–1456).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis* 92;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.* 1992;166:962–968).

Plasma immunoreactive endothelin-1 concentrations are elevated in patients with sepsis and correlate with the degree of illness and depression of cardiac output (Pittett J., et al., *Ann Surg.* 1991;213(3):262).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry* 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M. K., et al., *J. Hypertension* 1992;10(Suppl 4):S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci.* 1990;46:767).

The widespread localization of the endothelins and their receptors in the central nervous system and cerebrovascular circulation has been described (Nikolov R. K., et al., *Drugs of Today* 1992;28(5):303–310). Intracerebroventricular administration of ET-1 in rats has been shown to evoke several behavioral effects. These factors strongly suggest a role for the ETs in neurological disorders. The potent vasoconstrictor action of Ets on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (A. Lerman, et al., *New England J. Med.* 1991;325:997–1001). Increased endothelin immunoreactivity has also been associated with Buerger's disease (K. Kanno, et al., *J. Amer. Med. Assoc.* 1990;264:2868) and Raynaud's phenomenon (M. R. Zamora, et al., *Lancet* 1990;336:1144–1147).

An increase of circulating endothelin levels was observed in patients that underwent percutaneous transluminal coronary angioplasty (PTCA) (A. Tahara, et al., *Metab. Clin. Exp.* 1991;40:1235–1237).

Increased plasma levels of endothelin have been measured in rats and humans (Stewart, D. J., et al., *Ann. Internal Medicine* 1991;114:464–469) with pulmonary hypertension.

Elevated levels of endothelin have also been measured in patients suffering from ischemic heart disease (Yasuda, M., et al., *Amer. Heart J.* 1990;119:801–806) and either stable or unstable angina (Stewart, J. T., et al., *Br. Heart J.* 1991;66:7–9).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre, A., et al., *J. Physiology* 1991;444:513–522). In patients with chronic renal failure as well as in patients on regular hemodialysis treatment mean plasma endothelin levels were significantly increased (Stockenhuber, F., et al., *Clin. Sci. (Lond.)* 1992;82:255–258).

Local intra-arterial administration of endothelin has been shown to induce small intestinal mucosal damage in rats in a dose-dependent manner (Mirua, S., et al., *Digestion* 1991;48:163–172). Furthermore, it has been shown that an anti-ET-1 antibody reduced ethanol-induced vasoconstriction in a concentration-dependent manner (Masuda, E., et al., *Am. J. Physiol.* 1992;262:G785–G790). Elevated endothelin levels have been observed in patients suffering from Crohn's disease and ulcerative coliris (Murch, S. H., et al., *Lancet* 1992;339:381–384).

Recently at the 3rd International Conference on Endothelin, Houston, Tex., February 1993, the nonpeptide endothelin antagonist RO 46-2005 has been reported to be effective in models of acute renal ischemia and subarachnoid hemorrhage in rats (Clozel, M., et al., "Pathophysiological role of endothelin revealed by the first orally active endothelin receptor antagonist," *Nature*, 1993:365:759). In addition, the $ET_A$ antagonist BQ-123 has been shown to prevent early cerebral vasospasm following subarachnoid hemorrhage (Clozel, M. and Watanabe, H., *Life Sci.* 1993;52:825–834).

Most recently an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.*, 1994;37:329–331).

Furthermore, a specific $ET_A/ET_B$ receptor antagonist (see WO93 08799A1 and Elliott, J. D., et al., *J. Med. Chem.*, 1994; 37: 1553–7) has demonstrated reduced neointimal formation after angioplasty (Douglas, S. A., et al., *Circ. Res.*, 1994; 75:190–7).

TABLE I

Plasma Concentrations of ET-1 in Humans

| Condition | Normal Control | ET Plasma Levels Reported (pg/mL) |
|---|---|---|
| Atherosclerosis | 1.4 | 3.2pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure | 9.7 | 20.4 |

TABLE I-continued

Plasma Concentrations of ET-1 in Humans

| Condition | Normal Control | ET Plasma Levels Reported (pg/mL) |
|---|---|---|
| (CHF) | | |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
|  | 0.76 | 4.95 |
|  | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangio-endothelioma | 4.3 | 16.2 (after removal) |

Indoles and indolines have recently been reported as antagonists of endothelin in International Publication No. WO 94/14434. The present invention relates to certain indoles and indolines not previously described as potent antagonists of endothelin.

SUMMARY OF THE INVENTION

Accordingly, the present invention includes a compound of Formula I

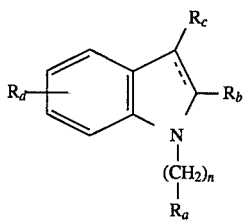

wherein denotes an optional bond;

n is 0–4;

$R_a$ is hydrogen, alkyl of 1–4 carbon atoms or cycloalkyl, phenyl or naphthyl, in which the phenyl or naphthyl group is substituted by methylenedioxy and further unsubstituted or substituted by one or more substituents selected from the group consisting of halogen, alkyl of 1–6 carbon atoms, OR, $NRR^1$, SR, $NO_2$, $N_3$, COR, $CO_2R$, $CONRR^1$, $SO_2NRR^2$, $SO_2R$, CN, $CF_3$, $CF_2CF_3$, CHO, $OCOCH_3$, B, $B(OH)_2$, phenyl, $NH(CH_2)_mCO_2R$, $S(CH_2)_mCO_2R$, $O(CH_2)_mCO_2R$, $O(CH_2)_mOR$, $NH(CH_2)_mOR$ and $S(CH_2)_mOR$, in which m is 1, 2 or 3, and R and $R^1$ are each independently hydrogen, alkyl of 1–4 carbon atoms, phenyl or benzyl;

$R_b$ is hydrogen, $CO_2R^2$,

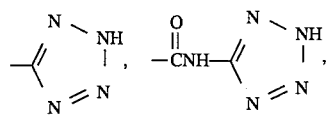

$SO_3R$, $PO_3H$, $B(OH)_2$, $CONR^1R^2$, $SO_2NR^1R^2$, or

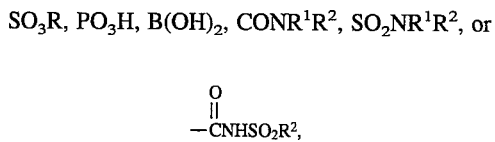

in which $R^1$ is as defined above and $R^2$ is hydrogen, alkyl of 1–6 carbon atoms, $CF_3$, $-CF_2CF_3$, phenyl or benzyl in which phenyl or the phenyl portion of the benzyl group is unsubstituted or substituted by one or more substituents as defined above;

$R_c$ is $S(O)_p$-phenyl, in which p is 0, 1 or 2, and phenyl is unsubstituted or substituted by one or more substituents selected from the group consisting of halogen, OR, $NRR^1$, SR, $NO_2$, $N_3$, COR, $CO_2R$, $CONRR^1$, $SO_2NRR^1$, $SO_2R$, CN, $CF_3$, $CF_2CF_3$, CHO, $OCOCH_3$, $B(OH)_2$, methylenedioxy, $O(CH_2)_mCO_2R$, $NH(CH_2)_mCO_2R$, $S(CH_2)_mCO_2R$, $O(CH_2)_mOR$, $NH(CH_2)_mOR$ and $S(CH_2)_mOR$, in which m, R and $R^1$ are as defined above, and $R_d$ is one to four independent substituents selected from hydrogen, alkyl of 1–7 carbon atoms, alkenyl of 2–7 carbon atoms, alkynyl of 2–7 carbon atoms, cycloalkyl, phenyl, C(O)-phenyl, X—$(CH_2)_n$-phenyl, X—$(CH_2)_n$-naphthyl, in which X is O, NH or $S(O)_p$, methylenedioxy, OR, $NRR^1$, SR, $NO_2$, $N_3$, COR, $CO_2R$, $CONRR^1$, $SO_2NRR^1$, $SO_2R$, CN, $CF_3$, $CF_2CF_3$, CHO, $OCOCH_3$, $B(OH)_2$, phenyl, $NH(CH_2)_mCO_2R$, $S(CH_2)_mCO_2R$, $O(CH_2)_mCO_2R$, $O(CH_2)_mOR$, NH$(CH_2)_mOR$, $S(CH_2)_mOR$, in which m is 1, 2 or 3 and R and $R^1$ are each independently hydrogen, alkyl of 1–4 carbon atoms, phenyl or benzyl and where n and p are as defined above and phenyl is unsubstituted or substituted as defined above, or a pharmaceutically acceptable acid addition or base salt thereof.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of essential renovascular malignant and pulmonary hypertension, cerebral infarction, diabetes, cerebral vasospasm, cirrhosis, septic shock, congestive heart failure, endotoxic shock, subarachnoid hemorrhage, arrhythmias, asthma, chronic and acute renal failure, preeclampsia, atherosclerotic disorders including Raynaud's disease and restenosis, angina, cancer, benign prosthetic hyperplasia, ischemic disease, gastric mucosal damage, hemorrhagic shock, and ischemic bowel disease. Particularly, the compounds of Formula I are useful in treating subarachnoid hemorrhage, hypertension, congestive heart failure, and cerebral ischemia and/or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as drowning, pulmonary surgery and cerebral trauma.

A still further embodiment of the present invention is a pharmaceutical composition for administering a therapeutically effective amount of a compound of Formula I in admixture with a pharmaceutically acceptable carrier in unit dosage form in the treatment methods mentioned above.

Finally, the present invention is directed to novel intermediates used for the production of compounds of Formula I.

DETAILED DESCRIPTION OF THE INVENTION

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl.

The term "alkenyl" means a straight or branched hydrocarbon radical having from 2 to 12 carbon atoms unless otherwise specified and having at least one double bond in the carbon atom chain and includes, for example, 1-ethene, 1-propene, 2-methyl-1-propene, 1-butene, 2-butene, 1-pentene, 2-pentene, 2-methyl-1-butene, 3-methyl-1-butene, 3-methyl-2-butene, 1-hexene, 1-heptene, 1-octene, 1-nonene, 1-decene, 1-undecene, 1-dodecene, and the like.

The term "alkynyl" means a straight or branched hydrocarbon radical having from 2 to 12 carbon atoms unless otherwise specified and having at least one triple bond in the carbon atom chain and includes, for example, 1-ethyne, 1-propyne, 1-butyne, 3-methyl-1-butyne, 1-pentyne, 2-pentyne, 1-hexyne, and the like.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl.

"Halogen" is fluorine, chlorine, bromine or iodine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M. et al., "Pharmaceutical Salts," "*Journal of Pharmaceutical Science* 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention, particularly, the dihydroindoles of Formula II and III, possess one or more chiral centers and each center may exist in the R or S configuration. The present invention includes all enantiomeric and epimeric forms as well as the appropriate diastereomeric mixtures thereof.

The compounds of the present invention include indoles that are partially saturated, i.e. indolines, wherein . . . in the compound of Formula I is an absent bond. These compounds may be illustrated by Formula II:

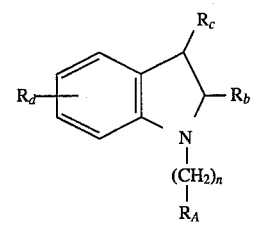

wherein n, $R_a$, $R_b$, $R_c$ and $R_d$ are as defined above.

Compounds of Formula I where . . . denotes a bond are best illustrated by the Formula III:

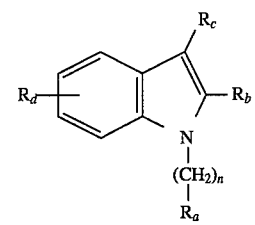

wherein n, $R_a$, $R_b$, $R_c$ and $R_d$ are as defined above.

Preferred embodiments of Formula I are compounds where $R_b$ is $CO_2R^2$ or

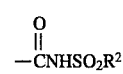

wherein $R^2$ is as defined above or, preferably, where $R^2$ is hydrogen, alkyl of 1–6 carbon atoms or phenyl.

A more preferred embodiment of a compound of Formula III is a compound of Formula IV:

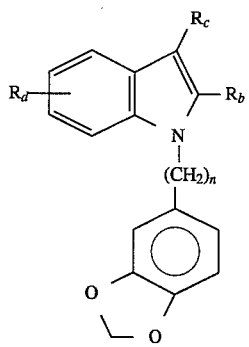

wherein $R_b$, $R_c$ and $R_d$ are as defined above, and n is 0 or 1.

A more preferred embodiment of Formula IV is a compound wherein $R_b$ and $R_c$ are as defined above, n is 0 or 1, and $R_d$ is methylenedioxy or one or two substituents selected from the group consisting of halogen, alkyl of 1–6 carbon atoms, OR, $NRR^1$, SR, $NO_2$, $N_3$, COR, $CO_2R$, CONHR, $SO_2NHR$, $SO_2R$, CN, $CF_3$, $CF_2CF_3$, CHO, $OCOCH_3$, $B(OH)_2$, phenyl, $NH(CH_2)_mCO_2R$, S $(CH_2)_mCO_2R$, $O(CH_2)_mCO_2R$, $O(CH_2)_mOR$, NH $(CH_2)_mOR$ and $S(CH_2)_mOR$, in which m is 1, 2 or 3, and R and $R^1$ are each independently hydrogen, alkyl of 1–4 carbon atoms, phenyl or benzyl. Most preferably also are compounds of Formula IV wherein $R_b$ is $CO_2H$, and $R_c$ is $S(O)_p$-phenyl, in which p is 0, 1 or 2, and phenyl is optionally substituted independently by methylenedioxy or one or more, preferably one to three methoxy, propoxy or benzyloxy groups. Still another most preferred embodiment are the above compounds of Formula IV wherein $R_d$ is methylenedioxy.

Particularly valuable are the following compounds.
1-benzo[1,3]dioxol-5-yl-3-phenylsulfanyl-1H-indole-2-carboxylic acid,
1-benzo[1,3]dioxol-5-ylmethyl-5,6-dimethoxy-3-(3-methoxy-phenylsulfanyl)- 1H-indole-2-carboxylic acid,
1-benzo[1,3]dioxol-5-ylmethyl-3-(3-methoxy-phenylsulfanyl)- 1H-indole-2-carboxylic acid,
1-benzyl-3-(3-methoxy-phenylsulfanyl)-1H-indole-2-carboxylic acid,
1-benzo[1,3]dioxol-5-ylmethyl-3-(benzo[ 1,3]dioxol-5-ylsulfanyl)-1H-indole-2-carboxylic acid,
5-benzo[1,3]dioxol-5-ylmethyl-7-(3-methoxy-phenylsulfanyl)- 5H-[1,3]dioxolo[4,5-f]indole-6-carboxylic acid,
5-(7-methoxy-benzo[1,3]dioxol-5-ylmethyl)-7-(3-methoxy-phenylsulfanyl)- 5H- [1,3]dioxolo [4,5-f]indole-6-carboxylic acid,
5-benzo[1,3]dioxol-5-ylmethyl-7-(3,4-dimethoxy-phenylsulfanyl)- 5H-[1,3]dioxolo[4,5-f]indole-6-carboxylic acid,
7-(3,4-dimethoxy-phenylsulfanyl)-5-(7-methoxy-benzo[ 1,3]dioxol-5-ylmethyl)-5H-[1,3]dioxolo[4,5-f]indole-6-carboxylic acid,
1-benzo[1,3]dioxol-5-ylmethyl-3-(3-methoxy-phenylsulfanyl)- 6-propoxy-1H-indole-2-carboxylic acid,
5,6-dimethoxy-1-(7-methoxy-benzo[1,3]dioxol-5-ylmethyl)- 3-(3-methoxy-phenylsulfanyl)-1H-indole-2-carboxylic acid,
5,6-dimethoxy-1-(4-methoxy-benzyl)-3-(3-methoxy-phenylsulfanyl)-1H-indole-2-carboxylic acid,
1-benzo[1,3]dioxol-5-ylmethyl-5-benzyloxy-6-methoxy-3-(3-methoxy-phenylsulfanyl)-1H-indole-2-carboxylic acid,
1-benzo[1,3]dioxol-5-ylmethyl-5,6-dimethoxy-3-( 3,4,5-trimethoxy-phenylsulfanyl)-1H-indole-2-carboxylic acid,
1-benzo[1,3]dioxol-5-ylmethyl-3-(benzo[ 1,3]dioxol-5-ylsulfanyl)-6-benzyloxy-5-methoxy- 1H-indole-2-carboxylic acid,
1-(2-carboxymethoxy-4-methoxy-benzyl)-5,6-dimethoxy-3-(3-methoxy-phenylsulfanyl)-1H-indole-2-carboxylic acid,
1-benzo[1, 3]dioxol-5-ylmethyl-3-(benzo[ 1,3 ]dioxol-5-ylsulfanyl)-5,6-dimethoxy-1H-indole- 2-carboxylic acid,
1-benzo[1,3]dioxol-5-ylmethyl-3-(3,4,5-trimethoxy-phenylsulfanyl)- 6-benzyloxy-5-methoxy- 1H-indole-2-carboxylic acid,
5-benzo[1,3]dioxol-5-ylmethyl-7- (3,4,5-trimethoxy-phenylsulfanyl)- 5H-[1,3]dioxolo[4,5-f]indole- 6-carboxylic acid, and
5-benzo[1,3]dioxol-5-ylmethyl-7-(benzo[ 1,3 ]dioxol-5-ylsulfanyl)-5H-[ 1,3]dioxolo [4,5-f]indole-6-carboxylic acid.

The compounds of Formula I are valuable antagonists of endothelin. The tests employed indicate that compounds of the invention possess endothelin antagonist activity. Thus, the compounds were tested for their ability to inhibit $[^{125}I]$ -ET-1($[^{125}I]$-Endothelin-1) binding in a receptor assay. Selected compounds were also tested for antagonist activity by inhibition of ET-1 stimulated arachidonic acid release and ET-1 stimulated vasoconstriction. The following testing procedures were used (Doherty, A. M., et al., "Design of C-Terminal Peptide Antagonists of Endothelin: Structure-Activity Relationships of ET-1 [16-21, D-His[16]]", *Bioorganic and Medicinal Chemistry Letters* 1993;3:497–502).

RADIOLIGAND BINDING ASSAYS

The following cultured cells were used in binding experiments: rabbit renal artery vascular smooth muscle cells (ERBA-A), Ltk-cells expressing recombinant human $ET_AR$ (HERBA-A), and CHO-K1 cells expressing recombinant human $ET_BR$ (HERBA-B).

Membranes were prepared from cultured cells by lysing cells in cold lysis buffer (5 mM HEPES, 2 mM EDTA, pH 7.4) and homogenizing with a Dounce "A" homogenizer. The homogenate was centrifuged at 30,000×g for 20 min at 4° C. Membrane pellets were suspended in cold buffer containing 20 mM Tris, 2 mM EDTA, 200 uM Pefabloc, 10 uM phosphoramidon, 10 uM leupeptin, 1 uM pepstatin at pH 7.4 and frozen at −80°C. until use. Membranes were thawed and homogenized with a Brinkmann Polytron then diluted in tissue buffer containing 20 mM Tris, 2 mM EDTA, 200 uM Pefabloc and 100 uM bacitracin (pH 7.4). Radioligand and competing ligands were prepared in binding buffer containing 20 mM Tris, 2 mM EDTA, and 0.1% BSA.

Competing binding assays were initiated by combining membranes, [125I]-ET-1 (40 pM) and the competing ligand in a final volume of 250 uL and incubating for 2 hours at 37° C. The assay was terminated by filtration over Whatman GF/B filters which were presoaked with 50 mM Tris, pH 7.4 containing 0.2% BSA and 100 uM bacitracin. Non specific binding was defined as binding in the presence of 100 nM ET-1.

IN VITRO INHIBITION OF ET-1 STIMULATED ARACHIDONIC ACID RELEASE (AAR) IN CULTURED RABBIT VASCULAR SMOOTH MUSCLE CELLS ($ET_A$) BY THE COMPOUNDS OF THE INVENTION

Antagonist activity is measured by the ability of added compounds to reduce endothelin-stimulated arachidonic acid release in cultured vascular smooth muscle cells as arachidonic acid release (AAR). [$^3$H] Arachidonic Acid Loading Media (LM) is DME/F12+0.5% FCS×0.25 mCi/ mL [$^3$H] arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 μL of scintillation cocktail was added, and the amount of [$^3$H] arachidonic acid was determined in a liquid scintillation counter.

IN VITRO ANTAGONISM OF ET-1 STIMULATED VASOCONSTRICTION (VERA-A) IN THE RABBIT FEMORAL ARTERY (ET$_A$) AND SARAFOTOXIN 6c STIMULATED VASOCONSTRICTION IN THE RABBIT PULMONARY ARTERY (ET$_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 gauge for femoral rings and 28 gauge for pulmonary rings, Small Parts, Inc, Miami, Fla.) and gently rolling them. Denuded rings were mounted in 20 mL organ baths containing Krebs-bicarbonate buffer (composition in mM: NaCl, 118.2; NaHCO$_3$, 24.8; KCl, 4.6; MgSO$_4$ 7.H$_2$O, 1.2; KH$_2$PO$_4$, 1.2; CACl$_2$.2H$_2$O; Ca-Na$_2$ EDTA, 0,026; dextrose, 10.0), that was maintained at 37° C. and gassed continuously with 5% CO$_2$ in oxygen (pH 7.4). Resting tension was adjusted to 3.0 g for femoral and 4.0 g pulmonary arteries; the rings were left for 90 minutes to equilibrate. Vascular rings were tested for lack of functional endothelium (i.e., lack of an endothelium-dependent relaxation response to carbachol (1.0 μM) in norepinephrine (0.03 μM) contracted rings. Agonist peptides, ET-1 (femoral), and S6c (pulmonary), were cumulatively added at 10-minute intervals. The ET antagonists were added 30 minutes prior to adding the agonist.

The data in Table II below show the endothelin receptor binding activity of representative compounds of the instant invention.

TABLE II

| | ACTIVITIES (IC$_{50}$, μm) | | | | |
|---|---|---|---|---|---|
| Example No. | VERA-A | ERBA-A | HERBA-A | VERA-B | HERBA-B |
| 1 | | 1.9 | 3.2 | | 6.5 |
| 2 | 7.0 | 0.03 | 0.02 | | 1.1 |

TABLE II-continued

| | ACTIVITIES (IC$_{50}$, μm) | | | | |
|---|---|---|---|---|---|
| Example No. | VERA-A | ERBA-A | HERBA-A | VERA-B | HERBA-B |
| 3 | | 0.50 | 0.09 | | 7.4 |
| 4 | | 7.3 | 4.6 | | 1.5 |
| 5 | | 0.57 | 0.38 | | 4.5 |
| 6 | | — | 0.084 | | 0.71 |
| 7 | | — | 0.38 | | 2.9 |
| 8 | 6.5 | — | 0.039 | 6.5 | 0.17 |
| 9 | | — | 0.17 | | 0.42 |
| 10 | | — | 0.59 | | 6.7 |
| 11 | | — | 0.058 | | 1.1 |
| 12 | | — | 0.16 | | 0.87 |
| 13 | | — | 0.081 | | 0.69 |
| 14 | 7.5 | — | 0.0015 | 5.5 | 0.25 |
| 15 | | | 0.69 | | 0.053 |
| 16 | | | 0.48 | | 1.2 |
| 17 | 7.3 | 6.2 | 0.0063 | | 0.033 |
| 18 | | | >2.5 | | >2.5 |

The compounds of Formula I may be prepared by several methods.

These methods are illustrated generally by way of scheme 1 illustrated below and in a detailed manner by way of illustration in the example section of the specification.

Scheme 1 illustrates the procedure used to synthesize 3-arylthioindoles. Indole-2-carboxylic acids are treated with diaryldisulphides in the presence of an excess of sodium hydride in DMF at 60° C. as described by Atkinson, J. G. et al., SyntheSiS, 1988, 480. The N-arylated derivative is then prepared by treatment with an aryl iodide or bromide in the presence of copper (II) oxide and KOH in DMF at 110° C. Alternatively treatment with trimethylsilyldiazomethane and then a benzylic halide in the presence of sodium hydride in DMF, affords the corresponding methylene homologue. Saponification is then affected with lithium hydroxide.

Starting materials, indole-2-carboxylic acids are either commercially available or prepared by known methods as described, for example, by Moody, C. J., *J. Chem. Soc. Perkin Trans*, 1, 1984, 1333, WO 91/09849 and Bande, F. J. et al., *Org. Synth. Coll.*, Vol. V, p. 567, 1973.

Finally, indolines may be prepared by reduction of the corresponding indoles as described by Pak, C. S., et al. *Tet. Lett.*, 1986, 27(21), 2409.

Alternatively, the reduction can be carried out with pyridinium borohydride on an indole where the nitrogen atom is not alkylated. The reduced indoline is then alkylated to form the final product. The reduction can be used to prepare indolines in general of the Formula II. Sodium cyanoborohydride may also be used to prepare indolines from indoles as described by Ketcha, D. M., et al., *Tet. Lett.*, 1989, 30(49), 6833.

SCHEME 1

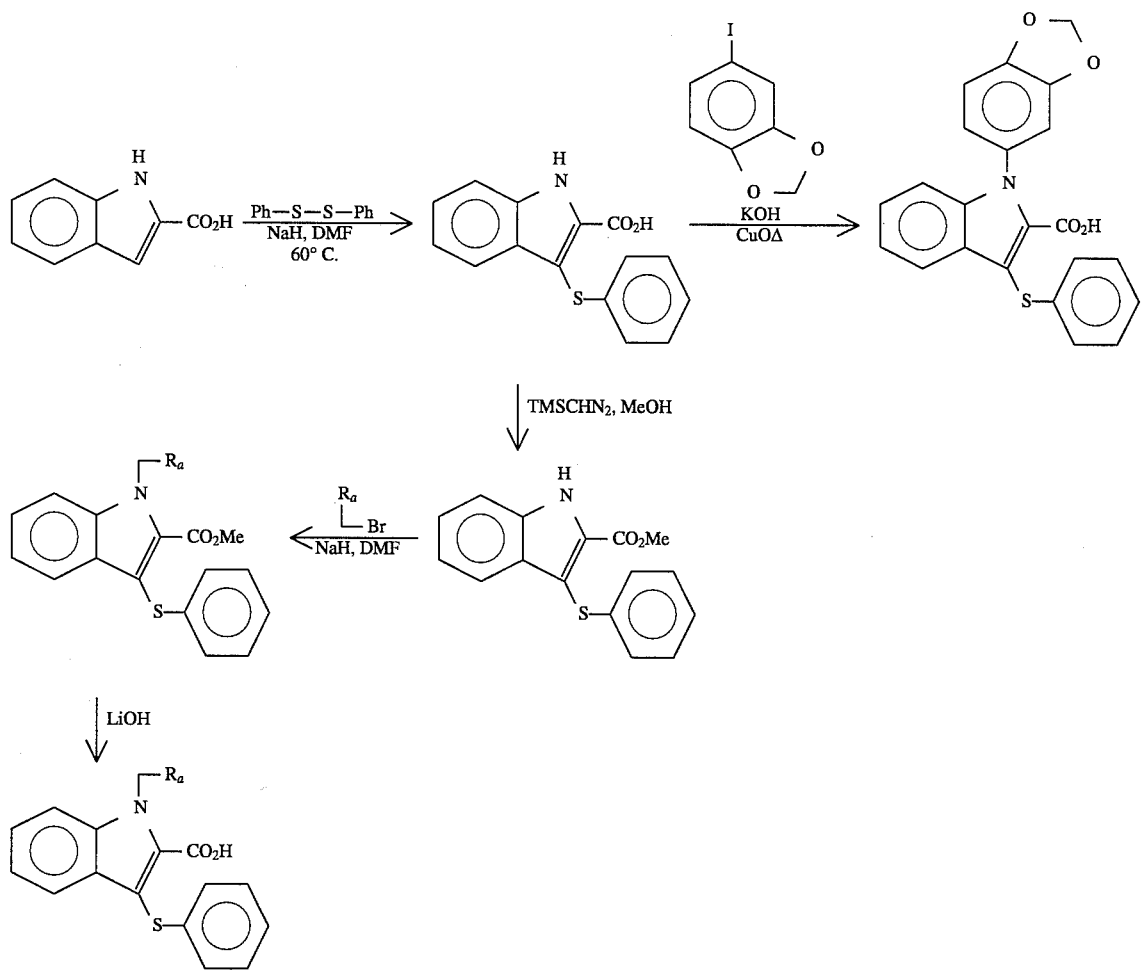

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulcse, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit: doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the preferred methods for preparing the compounds of the invention.

EXAMPLE 1

1-Benzo-[1,3]dioxol-5-yl-3-phenylsulfanyl-1H-indole-2 -carboxylic acid:

The title compound was prepared as shown in Scheme 1, using Indole-2-carboxylic acid (2.00 g, 0.0124 moles), phenyl disulfide (2.70 g, 0.0123 moles) and NaH (3 equiv.) in DMF (40 ml) at 60° C. for 16 hours. The adduct was dissolved in DMF, treated with copper(II) oxide (1 equiv.), 4-iodo-1,2-methylenedioxybenzene (1.3 equiv.) and KOH (2 equiv.). Heating for 16 hours at 110° C. afforded the required product. Analysis cal'd for C22H15NSO4: C, 67.85; H, 3.88; N, 3.60; found: C, 67.80; 3.87; N, 3.54. MS(CI) m/e 389. m.p. 182.0°–183.0° C.

EXAMPLE 2

1-Benzo-[1,3]dioxol-5-ylmethyl-5,6-dimethoxy-3-(3-methoxy-phenylsulfamyl)- 1H-indole-2-carboxylic acid:

The title compound was prepared as shown in Scheme 1, using 5,6-dimethoxy-indole- 2-carboxylic acid (0.4 g, 1.81 mmoles), di(3-methoxy) phenyl disulfide (0.65 g, 2.34 mmoles) and NaH (3 equiv.) in DMF (10 ml) at 60° C. for 16 hours. The adduct was dissolved in toluene (20 ml) and MeOH (5 ml) and treated with TMSdiazomethane (1 .5 equiv.) and then purified via column chromatography, eluting with chloroform. The required product was treated with NaH (1.2 equiv.), in DMF (3 ml), and 3,4-methylenedioxybenzyl chloride (1.25 equiv.). The product was isolated by chromatography after the reaction mixture had stirred for 16 hrs at room temperature. Saponification with lithium hydroxide (10 equiv.) at 40°–50° C. afforded the required product. Analysis cal'd for C26H23NSO7: C, 63.28; H, 4.70; N, 2.84; found: C, 63.24; H, 4.76; N, 2.87. MS(CI) m/e 493. m.p. 161°–2° C.

The following compounds were prepared according to the method of Example 2:

EXAMPLE 3

1-Benzo[1,3]dioxol-5-ylmethyl-3-(3-methoxy-phenylsulfanyl)- 1H-indole-2-carboxylic acid.

Analysis cal'd for C24H19NSO5: C, 66.50; H, 4.42; N, 3.23; found: C, 66.47; H, 4.51; N, 3.14. MS(CI) m/e 433. m.p. 168°–9° C.

EXAMPLE 4

1-Benzyl-3-(3-methoxy-phenylsulfanyl)-1H-indole-2carboxylic acid.

Analysis cal'd for C23H19O3NS: C, 70.93; H, 4.92; N, 3.60; found: C, 70.46, H, 4.91; N, 3.35. MS (CI) m/e 390. m.p. 186°–7° C.

EXAMPLE 5

1-Benzo[1,3]dioxol-5-ylmethyl-3-(benzo[1,3]dioxol- 5-ylsulfanyl)-1H-indole-2-carboxylic acid.

Analysis cal'd for C24H17O6NS: C, 64.42; H, 3.83; N, 3.13; found: C, 64.12; H, 3.77; N, 3.09. MS (CI) m/e 447 m.p. 188°–9° C.

EXAMPLE 6

5-Benzo[1,3]dioxol-5-ylmethyl-7-(3-methoxy-phenylsulfanyl)- 5H-[1,3]dioxolo[4,5-f]indole-6-carboxylic acid.

Analysis cal'd for C25H19O7NS: C, 62.89; H, 4.01; N, 2.93; found: C, 62.86; H, 4.03; N, 2.99. MS(CI) m/e 477. m.p. 186°–7° C.

EXAMPLE 7

5-(7-Methoxy-benzo[1,3]dioxol-5-ylmethyl)-7-(3-methoxy-phenylsulfanyl)- 5H-[1,3]dioxolo[4,5-f]indole-6carboxylic acid.

Analysis cal'd for C26H21O8NS: C, 61.53; H, 4.17; N, 2.76; found: C, 60.91; H, 4.20; N, 2.65. MS(CI) m/e 507. m.p. 164°–5° C.

EXAMPLE 8

5-Benzo [1,3 ]dioxo1-5-ylmethyl -7-(3,4-dimethoxyphenylsulfanyl)- 5H-[1,3]dioxolo[4,5-f]indole-6-carboxylic acid.

Analysis cal'd for C26H21O8NS: C, 61.53; H, 4.17; N, 2.76; found: C, 61.50; H, 4.23; N, 2.73. MS(CI) m/e 507. m.p. 174°–5° C.

EXAMPLE 9

7-(3,4-Dimethoxy-phenylsulfanyl)-5-(7-methoxy-benzo[1,3]dioxol-5-ylmethyl)-5H-[1,3]dioxolo[4,5-f]indole- 6-carboxylic acid.

Analysis cal'd for C27H23O9NS: C, 60.33; H, 4.31; N, 2.61; found: C, 60.10; H, 4.18; N, 2.48. MS (CI) m/e 493. m.p. 183°–4°C.

EXAMPLE 10

1-Benzo[1,3]dioxol-5-ylmethyl-3-(3-methoxy-phenylsulfanyl)- 6-propoxy-1H-indole-2-carboxylic acid.

Analysis cal'd for C27H25NO6S: C, 65.97; H, 5.13; N, 2.85; found: C, 65.75; H, 5.29; N, 2.95. MS(CI) m/e 491. m.p. 145°–6° C.

EXAMPLE 11

5,6-Dimethoxy-1-(7-methoxy-benzo[1,3]dioxol-5-ylmethyl)- 3-(3-methoxy-phenylsulfanyl)-1H-indole-2carboxylic acid.

Analysis cal'd for C27H25NO8S: C, 61.94; H, 4.81; N, 2.68; found: C, 61.71; H, 4.87; N, 2.58. MS(CI) m/e 523. m.p. 165°–6°C.

EXAMPLE 12

5,6-Dimethoxy-1-(4-methoxy-benzyl)-3-(3-methoxy-phenylsulfanyl)- 1H-indole-2-carboxylic acid.

Analysis cal'd for C26H25NO6S: C, 65.12; H, 5.25; N, 2.92; found: C, 64.78; H, 5.26; N, 2.96. MS(CI) m/e 479. m.p. 163°–4°C.

EXAMPLE 13

1-Benzo[1,3]dioxol-5-ylmethyl-5-benzyloxy-6-methoxy-3-(3-methoxy-phenylsulfanyl)-1H-indole-2-carboxylic acid.

Analysis cal'd for C32H27NO7S: C, 67.47; H, 4.78; N, 2.46; found: C, 67.28; H, 4.92; N, 2.33. MS(CI) m/e 569. m.p. 166°–167° C.

EXAMPLE 14

1-Benzo[1,3]dioxol-5-ylmethyl-5,6-dimethoxy-3-( 3,4,5-trimethoxy-phenylsulfanyl)-1H-indole-2-carboxylic acid.

Analysis cal'd for C28H27NO9S: C, 60.75; H, 4.92; N, 2.53; found: C, 60.64; H, 4.84; N, 2.50. MS(CI) m/e 511. m.p. 177°–178° C.

EXAMPLE 15

1-Benzo[1,3]dioxol-5-ylmethyl-3-(benzo[1,3]dioxol-5-ylsulfanyl)- 6-benzyloxy-5-methoxy-1H-indole -2-carboxylic acid.

Analysis calc'd for C32H25NO8S: C, 65.86; H, 4.32; N, 2.40; found: C, 66.16; H, 4.60; N, 2.28. MS(CI) m/e 583. m.p. 170°–171° C.

EXAMPLE 16

1-(2-Carboxymethoxy-4-methoxy-benzyl)-5,6-dimethoxy-3-(3-methoxy-phenylsulfanyl)-1H-indole-2carboxylic acid.

Analysis calc'd for C28H27NO9S: C, 60.75; H, 4.92; N, 2.53; found: C, 59.68; H, 4.97; 2.36. MS(CI) m/e 553. m.p. 160°–161° C.

EXAMPLE 17

1-Benzo[1,3]dioxol-5-ylmethyl-3-(benzo[1,3]dioxol-5-ylsulfanyl)- 5,6-dimethoxy-1H-indole-2-carboxylic acid.

Analysis cal'd for C26H21NO8S: C, 61.53; H, 4.17; N, 2.76; found: C, 61.18; H, 4.15; N, 2.66. MS(CI) m/e 507. m.p. 214°–215° C.

EXAMPLE 18

1-Benzo[1,3]dioxol-5-ylmethyl-3-(3,4,5-trimethoxy-phenylsulfanyl)- 6-benzyloxy-5-methoxy-1H-indole-2-carboxylic acid.

Analysis cal'd for C34H31NO9S: C, 64.85; H, 4.96; N, 2.22; found: C, 64.89; H, 5.04; N, 2.03. MS(CI) m/e 629. m.p. 162°–3° C.

EXAMPLE 19

Benzene, 1,1'-dithiobis 3,4,5-trimethoxy-.

According to the general procedure as described in Takagi, K. Synthesis of Aromatic thiols from aryiodides and thiourea by means of nickel catalyst. *Chem. Lett.* 1985, 1307–1308.

To a solution of 1-iodo-3,4,5-trimethoxybenzene (13.56 g, 46.12 mmoles) in DMF (75 ml) was added thiourea (5.27 g, 69.2 mmoles), bis(triethylphosphine) nickel (II) chloride (1.70 g, 4.62 mmoles) and sodium cyanoborohydride (0.44 g, 6.99 mmoles). The mixture was heated at 60° C. for 16 hours. To the mixture at room temperature was added sodium hydroxide (1N, 130 ml) and air was bubbled through the mixture for 24 hours. The precipitated solid was collected by filtration and washed with water. Crystallization from ethylacetate, after filtering through celite, afforded 3,4,5-trimethoxybenzene disulphide (4.63 g, 50%) as light yellow crystals. Analysis calc'd for C18H22O6S2: C, 54.25; H, 5.56; found: C, 53.72; H, 5.18. MS(CI) m/e 398. m.p. 143°–144° C.

EXAMPLE 20

1,3-Benzodioxole, 5,5'-dithiobis-.

The title compound was prepared according to Example 19 from 1-iodo-3,4-methylenedioxybenzene. Analysis cal'd for C14H10O4S2: C, 54.89; H, 3.29; found: C, 55.01; H, 3.35. MS(CI) m/e 306. m.p. 53°–54° C.

What is claimed is:
1. A compound of the formula

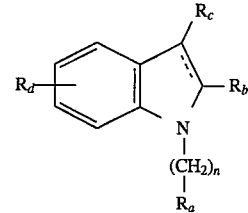

wherein

- - - denotes an optional bond;

n is 0–4;

$R_a$ is phenyl, in which the phenyl group is substituted by methylenedioxy and further unsubstituted or substituted by one or more substituents selected from the group consisting of halogen, alkyl of 1–6 carbon atoms, OR, NRR$^1$, SR, NO$_2$, N$_3$, COR, CO$_2$R, CONRR$^1$, SO$_2$NRR$^1$, SO$_2$R, CN, CF$_3$, CF$_2$CF$_3$, CHO, OCOCH$_3$, B(OH)$_2$, phenyl, NH(CH$_2$)$_m$CO$_2$R, S(CH$_2$)$_m$CO$_2$R, O(CH$_2$)$_m$CO$_2$R, O(CH$_2$)$_m$OR, NH(CH$_2$)$_m$OR and S(CH$_2$)$_m$OR, in which m is 1, 2 or 3, and R and R$^1$ are each independently hydrogen, alkyl of 1–4 carbon atoms, phenyl or benzyl;

$R_b$ is hydrogen, $CO_2R^2$,

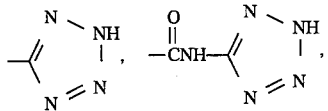

$SO_3R$, $PO_3H$, $B(OH)_2$, $CONR^1R^2$, $SO_2NR^1R^2$, or

in which R and $R^1$ are as defined above and $R^2$ is hydrogen, alkyl of 1–6 carbon atoms, $CF_3$, —$CF_2CF_3$, phenyl or benzyl in which phenyl or the phenyl portion of the benzyl group is unsubstituted or substituted by one or more substituents as defined in $R_a$ above;

$R_c$ is $S(O)_p$-phenyl, in which p is 0, 1 or 2, and phenyl is unsubstituted or substituted by one or more substituents selected from the group consisting of halogen, OR, $NNR^1$, SR, $NO_2$, $N_3$, COR, $CO_2R$, $CONRR^1$, $SO_2NNR^1$, $SO_2R$, CN, $CF_3$, $CF_2CF_3$, CHO, $OCOCH_3$, $B(OH)_2$, methylenedioxy, $NH(CH_2)_mCO_2R$, $S(CH_2)_mCO_2R$, $O(CH_2)_mCO_2R$, $O(CH_2)_mOR$, $NH(CH_2)_mOR$ and $S(CH_2)_mOR$, in which m, R and $R^1$ are as defined above, and $R_d$ is one to four independent substituents selected from hydrogen, alkyl of 1–7 carbon atoms, alkenyl of 2–7 carbon atoms, alkynyl of 2–7 carbon atom, cycloalkyl, phenyl, C(O)-phenyl, $X(CH_2)_n$-phenyl, $X-(CH_2)_n$-naphthyl, in which X is O, NH or $S(O)_p$, methylenedioxy, OR, $NNR^1$, SR, $NO_2$, $N_3$, COR, $CO_2R$, $CONRR^1$, $SO_2R$, $SO_2R$, CN, $CF_3$, $CF_2CF_3$, CHO, $OCOCH_3$, $B(OH)_2$, phenyl, $NH(CH_2)_mCO_2R$, $S(CH_2)_mCO_2R$, $O(CH_2)_mCO_2R$, $O(CH_2)_mOR$, $NH(CH_2)_mOR$, $S(CH_2)_mOR$, in which m is 1, 2 or 3 and R and $R^1$ are each independently hydrogen, alkyl of 1–4 carbon atoms, phenyl or benzyl and where n and p are as defined above and phenyl is unsubstituted or substituted as defined in $R_c$ above, or a pharmaceutically acceptable acid addition or base salt thereof.

2. A compound of claim 1 of the formula

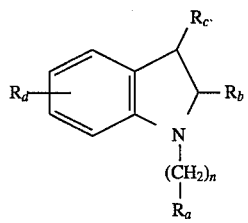

wherein n, $R_a$, $R_b$, $R_c$ and $R_d$ are as defined in claim 1 above.

3. A compound of claim 1 and of the formula

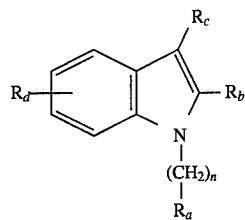

wherein n, $R_a$, $R_b$, $R_c$ and $R_d$ are as defined in claim 1 above.

4. A compound of claim 1 wherein $R_b$ is $CO_2R^2$ or

5. A compound of claim 4 wherein $R^2$ is hydrogen, alkyl of 1–6 carbon atoms or phenyl.

6. A compound of claim 5 and of the formula

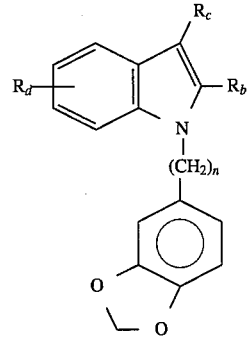

wherein n is 0 or 1, and $R_b$, $R_c$ and $R_d$ are as defined in claim 1 above.

7. A compound of claim 6, wherein $R_d$ is methylenedioxy or one or two substituents selected from the group consisting of halogen, alkyl of 1–6 carbon atoms, OR, $NRR^1$, SR, $NO_2$, $N_3$, COR, $CO_2R$, CONHR, $SO_2NHR$, $SO_2R$, CN, $CF_3$, $CF_2CF_3$, CHO, $OCOCH_3$, $B(OH)_2$, phenyl, $NH(CH_2)_mCO_2R$, $S(CH_2)_mCO_2R$, $O(CH_2)_mCO_2R$, $O(CH_2)_mOR$, $NH(CH_2)_mOR$ and $S(CH_2)_mOR$, in which m is 1, 2 or 3, and R and $R^1$ are each independently hydrogen, alkyl of 1–4 carbon atoms, phenyl or benzyl.

8. A compound of claim 7, wherein $R_b$ is $CO_2H$ and $R_c$ is $S(O)_p$-phenyl, in which p is 0, 1 or 2, and phenyl is unsubstituted or substituted independently by methylenedioxy or one to three methoxy, propoxy or benzyloxy groups.

9. A compound of claim 8, wherein $R_d$ is methylenedioxy.

10. A compound selected from the group consisting of 1-benzo[1,3]dioxol-5-yl-3-phenylsulfanyl-1H-indole-2-carboxylic acid, 1-benzo[1,3]dioxol-5-ylmethyl- 3-(3-methoxy-phenylsulfanyl)-1H-indole-2-carboxylic acid, 1-benzo[1,3]dioxol-5-ylmethyl-3(benzo[1,3]dioxol-5-ylsulfanyl)-1H-indole-2-carboxylic acid, 1-benzo[1,3]dioxol-5-ylmethyl-3-(3-methoxy-phenylsulfanyl)- 6-propoxy-1H-indole-2-carboxylic acid, 5,6-dimethoxy-1-(7-methoxy-benzo[1,3]dioxol-5-ylmethyl)-3-(3-methoxy-phenylsulfanyl)-1H-indole-2-carboxylic acid, 5,6-dimethoxy-1-(4-methoxy-benzyl)-3-(3-methoxy-phenylsulfanyl)- 1H-indole-2-carboxylic acid, 1benzo[1,3]dioxol-5-ylmethyl-5-benzyloxy-6-methoxy-3-(3-methoxy-phenylsulfanyl)- 1H-indole-2-carboxylic acid, 1benzo[1,3]

dioxol-5-ylmethyl-3-(benzo[1,3]dioxol-5-ylsulfanyl)-6-benzyloxy-5-methoxy-1H-indole-2-carboxylic acid, 1-(2-carboxymethoxy-4-methoxy-benzyl)-5,6-dimethoxy- 3-(3-methoxy-phenylsulfanyl)-1H-indole-2carboxylic acid, 1-benzo[1,3]dioxol-5-ylmethyl-3(benzo[1,3]dioxol-5-ylsulfanyl)-5,6-dimethoxy-1H-indole-2-carboxylic acid, and 1-benzo[1,3]dioxol-5-ylmethyl-3-( 3,4,5-trimethoxy-phenylsulfanyl ) -6-benzyloxy-5-methoxy- 1H-indole-2-carboxylic acid.

11. The compound 1-benzo[1,3 ]dioxol-5-ylmethyl-5,6-dimethoxy-3-(3-methoxy-phenylsulfanyl)- 1H-indole-2-carboxylic acid.

12. The compound 1-benzo[1,3 ]dioxol-5-ylmethyl-5,6-dimethoxy-3-(3,4,5-trimethoxy-phenylsulfanyl)- 1H-indole-2-carboxylic acid.

13. A compound selected from the group consisting of 5-benzo[1,3]dioxol-5-ylmethyl-7-(3-methoxy-phenylsulfanyl)- 5H-[1,3]dioxolo[4,5-f]indole-6-carboxylic acid, 5-(7-methoxy-benzo[1,3]dioxol-5-ylmethyl)- 7-(3-methoxy-phenylsulfanyl)-5H[1,3]dioxolo[4,5-f]indole-6-carboxylic acid, 5benzo[1,3]dioxol-5-ylmethyl-7-(3,4-dimethoxy-phenylsulfanyl)-5H-[ 1,3]dioxolo[4,5-f]indole-6-carboxylic acid, and 7-(3,4-dimethoxy-phenylsulfanyl)-5-(7-methoxy-benzo[1,3]dioxol-5-ylmethyl)-5H-[1,3]dioxolo[4,5-f]indole-6-carboxylic acid.

14. The compound 5-benzo[1,3]dioxol-5-ylmethyl-7-(3,4,5-trimethoxy-phenylsulfanyl)- 5H-[1,3]dioxolo[4,5-f]indole-6-carboxylic acid or 5-benzo[1,3]dioxol-5-ylmethyl-7-(benzo[1,3]dioxol-5-ylsulfanyl)-5H-[1,3]dioxolo [4,5-f] indole-6-carboxylic acid.

15. A pharmaceutical composition comprising a therapeutically effective amount of a compound of claim 1 in admixture with a pharmaceutically acceptable carrier.

16. A method of inhibiting elevated levels of endothelin comprising administering to a host in need thereof a therapeutically effective amount of a compound of claim 1 in unit dosage form.

17. A method of treating subarachnoid hemorrhage comprising administering to a host suffering therefrom a therapeutically effective amount of a compound of claim 1 in unit dosage form.

18. A method of treating essential renovascular malignant and pulmonary hypertension comprising administering to a host suffering therefrom a therapeutically effective amount of a compound of claim 1 in unit dosage form.

19. A method of treating congestive heart failure comprising administering to a host suffering therefrom a therapeutically effective amount of a compound of claim 1 in unit dosage form.

20. A method of treating cerebral ischemia or cerebral infarction comprising administering to a host suffering therefrom a therapeutically effective amount of a compound of claim 1 in unit dosage form.

* * * * *

UNITED STATES PATENT AND TRADEMARK OFFICE
CERTIFICATE OF CORRECTION

PATENT NO. : 5,482,960
DATED : January 9, 1996
INVENTOR(S) : Berryman, et al.

It is certified that error appears in the above-indentified patent and that said Letters Patent is hereby corrected as shown below:

Column 19, line 29, at the beginning of the line, delete " $NNR^1$, " and insert instead -- $NRR^1$, -- .

Column 19, line 41, delete " $NNR^1$, " and insert instead -- $NRR^1$, -- .

Column 19, line 42, delete the first " $SO_2R$, " and insert instead -- $SO_2NRR^1$, -- .

Column 20, line 65, at the end of the line, insert a hyphen between the " 1 " and " benzo[1,3] " .

Column 20, last line, at the end of the line, insert a hyphen between the " 1 " and " benzo[1,3] " .

Column 21, line 4, insert a hyphen between " 2 " and " carboxylic " .

UNITED STATES PATENT AND TRADEMARK OFFICE
CERTIFICATE OF CORRECTION

PATENT NO. : 5,482,960
DATED : January 9, 1996
INVENTOR(S) : Berryman et al

It is certified that error appears in the above-indentified patent and that said Letters Patent is hereby corrected as shown below:

Column 21, line 5, insert a hyphen between " 3 " and " (benzo " .

Column 21, line 21, at the beginning of the line, insert a hyphen after the " 5 " .

Signed and Sealed this

Ninth Day of April, 1996

Attest:

BRUCE LEHMAN

Attesting Officer

Commissioner of Patents and Trademarks